(12) United States Patent
Barbato et al.

(10) Patent No.: US 8,423,110 B2
(45) Date of Patent: Apr. 16, 2013

(54) IMAGING DEVICE AND RELATED METHODS

(75) Inventors: Louis J. Barbato, Franklin, MA (US);
Robert J. Crowley, Sudbury, MA (US);
Yem Chin, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2786 days.

(21) Appl. No.: 10/195,603

(22) Filed: Jul. 15, 2002

(65) Prior Publication Data

US 2003/0130562 A1 Jul. 10, 2003

Related U.S. Application Data

(60) Provisional application No. 60/347,391, filed on Jan. 9, 2002.

(51) Int. Cl.
*A61B 5/00* (2006.01)

(52) U.S. Cl.
USPC .............................. 600/342; 600/310; 600/407

(58) Field of Classification Search .................. 600/407, 600/424, 310, 342; 356/402, 406; 359/618
See application file for complete search history.

(56) References Cited

U.S. PATENT DOCUMENTS

| | | | |
|---|---|---|---|
| 4,265,121 A | 5/1981 | Cribbs | 73/607 |
| 4,340,307 A | 7/1982 | Diamond et al. | 356/418 |
| RE31,289 E | 6/1983 | Moore et al. | 128/6 |
| 4,510,384 A * | 4/1985 | Grimbleby et al. | 250/201.7 |
| 4,541,272 A | 9/1985 | Bause | 73/118 |
| 4,563,087 A * | 1/1986 | Bourbin et al. | 356/73.1 |
| 4,674,844 A * | 6/1987 | Nishioka et al. | 359/782 |

(Continued)

FOREIGN PATENT DOCUMENTS

| | | |
|---|---|---|
| DE | 100 41 878 | 4/2001 |
| FR | 2 666 713 | 3/1992 |

(Continued)

OTHER PUBLICATIONS

Hit Lab Research website, "Engineering Study of an Endoscope Design," *Human Interface Lab of University of Washington*, <http://www.hitl.washington.edu/research/endoscope>, 2 pages, dated Apr. 14, 1998, (downloaded Sep. 16, 2001).

(Continued)

*Primary Examiner* — Long V. Le
*Assistant Examiner* — Ellsworth Weatherby
(74) *Attorney, Agent, or Firm* — Bookoff McAndrews, PLLC

(57) ABSTRACT

In one embodiment, the invention provides an imaging device having a light source, a photo-sensor and a scanning assembly. In some embodiments, the light source is fixedly mounted in the first end of an elongated sheath and is adapted for illuminating a target, and the photo-sensor is mounted on the scanning assembly, also in the first end of the elongated sheath, and is adapted to detect light energy from the target. In other embodiments, the light source is movably mounted and the detector is held stationary. In other embodiments, both the light source and the photo-sensor are movably mounted. The scanning devices synchronously capture light energy from each of a plurality of locations on the target, the light energy resulting from illumination by the light source, and synchronously digitizes the output from the photo-sensor from each of the plurality of locations on the target to generate an image of the target.

23 Claims, 13 Drawing Sheets

U.S. PATENT DOCUMENTS

| | | | |
|---|---|---|---|
| 4,718,417 A | 1/1988 | Kittrell et al. | 128/303.1 |
| 4,736,734 A | 4/1988 | Matsuura et al. | 128/6 |
| 4,803,992 A * | 2/1989 | Lemelson | 600/342 |
| 4,854,302 A | 8/1989 | Allred, III | 128/6 |
| 4,895,156 A | 1/1990 | Schulze | 128/634 |
| 4,895,431 A * | 1/1990 | Tsujiuchi et al. | 359/29 |
| 4,898,175 A | 2/1990 | Noguchi | 128/634 |
| 4,923,263 A | 5/1990 | Johnson | 350/6.9 |
| 4,934,340 A | 6/1990 | Ebling et al. | 128/6 |
| 4,981,138 A | 1/1991 | Deckelbaum et al. | 128/665 |
| 5,001,556 A | 3/1991 | Nakamura et al. | 358/98 |
| 5,042,494 A | 8/1991 | Alfano | 128/665 |
| 5,051,823 A | 9/1991 | Cooper et al. | 358/98 |
| 5,106,387 A | 4/1992 | Kittrell et al. | 606/15 |
| 5,120,953 A | 6/1992 | Harris | |
| 5,131,398 A | 7/1992 | Alfano et al. | 128/665 |
| RE34,110 E | 10/1992 | Opie et al. | 128/6 |
| 5,159,446 A | 10/1992 | Hibino et al. | |
| 5,160,837 A | 11/1992 | Hirane et al. | 250/208.2 |
| 5,187,572 A | 2/1993 | Nakamura et al. | 358/98 |
| 5,200,838 A * | 4/1993 | Nudelman et al. | 358/443 |
| 5,217,454 A * | 6/1993 | Khoury | 606/7 |
| 5,241,170 A | 8/1993 | Field, Jr. et al. | |
| 5,309,907 A | 5/1994 | Fang et al. | 128/633 |
| 5,313,306 A | 5/1994 | Kuban et al. | 348/65 |
| 5,318,024 A | 6/1994 | Kittrell et al. | 128/634 |
| 5,377,676 A | 1/1995 | Vari et al. | 128/634 |
| 5,391,352 A * | 2/1995 | Hendrix et al. | 422/65 |
| 5,402,801 A | 4/1995 | Taylor | 128/898 |
| 5,408,998 A | 4/1995 | Mersch | 128/633 |
| 5,414,683 A | 5/1995 | Tani | |
| 5,417,207 A | 5/1995 | Young et al. | 128/634 |
| 5,417,210 A | 5/1995 | Funda et al. | 128/653.1 |
| 5,429,616 A | 7/1995 | Schaffer | 604/250 |
| 5,434,940 A | 7/1995 | Roff et al. | 385/91 |
| 5,467,104 A | 11/1995 | Furness, III et al. | 345/8 |
| 5,467,767 A | 11/1995 | Alfano et al. | 128/665 |
| 5,517,997 A | 5/1996 | Fontenot | 128/664 |
| 5,537,213 A * | 7/1996 | Seim et al. | 356/406 |
| 5,540,691 A | 7/1996 | Elstrom et al. | 606/64 |
| 5,557,444 A | 9/1996 | Melville et al. | 359/199 |
| 5,596,988 A | 1/1997 | Markle et al. | 128/635 |
| 5,601,087 A | 2/1997 | Gunderson et al. | 128/664 |
| 5,626,139 A | 5/1997 | Szeles et al. | 128/664 |
| 5,701,132 A | 12/1997 | Kollin et al. | 345/8 |
| 5,715,825 A | 2/1998 | Crowley | 128/602.06 |
| 5,730,134 A | 3/1998 | Dumoulin et al. | 128/653.1 |
| 5,762,603 A | 6/1998 | Thompson | |
| 5,792,053 A * | 8/1998 | Skladnev et al. | 600/407 |
| 5,800,478 A | 9/1998 | Chen et al. | 607/88 |
| 5,829,878 A | 11/1998 | Weiss et al. | 374/163 |
| 5,831,181 A * | 11/1998 | Majumdar et al. | 73/863 |
| 5,851,181 A * | 12/1998 | Talmor | 600/407 |
| 5,885,293 A | 3/1999 | McDevitt | 606/80 |
| 5,928,137 A | 7/1999 | Green | 600/160 |
| 5,951,480 A | 9/1999 | White et al. | 600/463 |
| 5,984,861 A | 11/1999 | Crowley | 600/175 |
| 5,989,231 A | 11/1999 | Snow et al. | 604/264 |
| 5,994,713 A * | 11/1999 | Becker et al. | 250/591 |
| 6,017,312 A | 1/2000 | Masters | 600/462 |
| 6,042,555 A * | 3/2000 | Kramer et al. | 600/595 |
| 6,074,349 A | 6/2000 | Crowley | 600/463 |
| 6,096,065 A | 8/2000 | Crowley | 607/88 |
| 6,119,031 A | 9/2000 | Crowley | 600/407 |
| 6,140,979 A | 10/2000 | Gerhard et al. | 345/7 |
| 6,151,167 A | 11/2000 | Melville | 359/618 |
| 6,165,127 A | 12/2000 | Crowley | 600/463 |
| 6,174,291 B1 | 1/2001 | McMahon et al. | 600/564 |
| 6,174,307 B1 | 1/2001 | Daniel et al. | 606/15 |
| 6,185,443 B1 * | 2/2001 | Crowley | 600/407 |
| 6,238,348 B1 | 5/2001 | Crowley et al. | 600/476 |
| 6,256,131 B1 | 7/2001 | Wine et al. | 359/199 |
| 6,289,229 B1 | 9/2001 | Crowley | 600/310 |
| 6,294,775 B1 | 9/2001 | Seibel et al. | 250/208.1 |
| 6,324,007 B1 | 11/2001 | Melville | 359/618 |
| 6,324,418 B1 | 11/2001 | Crowley et al. | 600/476 |
| 6,331,909 B1 | 12/2001 | Dunfield | 359/199 |
| 6,498,948 B1 | 12/2002 | Ozawa et al. | |
| 6,622,547 B1 * | 9/2003 | Phan et al. | 73/105 |
| 7,129,472 B1 | 10/2006 | Okawa et al. | |
| 2001/0055462 A1 * | 12/2001 | Seibel | 385/147 |
| 2002/0064341 A1 * | 5/2002 | Fauver et al. | 385/25 |

FOREIGN PATENT DOCUMENTS

| | | |
|---|---|---|
| JP | 60-217327 | 10/1985 |
| JP | 63-040117 | 2/1988 |
| JP | 7-289506 A | 11/1995 |
| JP | 11-298803 | 10/1999 |
| JP | 2001-174744 | 6/2001 |
| JP | 2001-290100 | 10/2001 |
| WO | 94/13191 A1 | 6/1994 |
| WO | 98/22034 A2 | 5/1998 |
| WO | 98/22184 A1 | 5/1998 |
| WO | 98/22805 A1 | 5/1998 |
| WO | 99/16344 A1 | 4/1999 |
| WO | 01/19235 A1 | 3/2001 |

OTHER PUBLICATIONS

Microvision, Inc. "Imaging Solutions," <http://web.archive.org/web/20010809170139/http://www.mvis.com/imagingsol.htm>, 6 pages, (downloaded Aug. 9, 2001 archived website), Copyright 2000.

Microvision 10Q (SEC) filed Aug. 14, 2001, <http://hoovnews.tenkwizard.com/filing.php?repo=tenk&ipage=1474067&doc=1&total=&back=1&g=&attach=on>, 6 pages.

Seibel, "Engineering Study of a Novel Design for a Scanned, Single Fiber Endoscope," *Investigator Abstracts Biomedical Engineering*, <http://www.whitaker.org>, 1 page, (downloaded Sep. 26, 2001).

Smithwick et al., "Unique Features of the Scanning Single Fiber Endoscope", *Human Interface Technology Laboratory at the University of Washington*, 35 pages, Oct. 25, 2001.

Urey et al., "Scanner Design and Resolution Tradeoffs for Miniature Scanning Displays," *Microvision Inc.*, <http://www.mvis.com>, 12 pages, (downloaded Oct. 4, 2001), Copyright 2000.

Urey et al., "Scanner Design and Resolution Tradeoffs for Miniature Scanning Displays," *Microvision Inc.*, <http://www.web.archive.org/web/20010814233519/www.mvis.com/whitepapers_scannerdesigns.htm, 22 pages, (downloaded Aug. 14, 2001 archived website), Copyright 2000.

* cited by examiner

IMAGING DEVICE AND RELATED METHODS

RELATED APPLICATION

This application is based on prior provisional patent application Ser. No. 60/347,391, filed on Jan. 9, 2002, the benefit of the filing date of which is hereby claimed under 35 U.S.C. §119(e).

TECHNICAL FIELD

This invention relates to imaging devices. More particularly, in one embodiment, the invention is directed to a miniature imaging device and related methods.

BACKGROUND OF THE INVENTION

Spectral analysis of living tissue can be used to detect various forms of cancer and other types of diseases. In spectral analysis, light illuminates a tissue region under examination and a light detector detects optical properties of the illuminated tissue region by measuring light energy modified by its interaction with the tissue region in a pre-determined frequency and amplitude domain. Optical properties include absorption, luminescence, fluorescence, frequency and time domain response to various materials injected to the tissue region and other electromagnetic responses. Diseased tissue may be identified by comparing a spectrum obtained to spectra of normal tissue obtained under the same controlled conditions.

Traditional image sensors include a two dimensional array of photo-detectors (pixels) that are accessed individually by electronics on the same chip, or external to the chip. A black and white image is formed by digitizing the amplitude of each pixel, which creates a gray scale. Color images function in a similar manner, but employ complex algorithms to compute the color. One common color sensor has a color mask that is placed on the image sensor. The color mask is a light filter that allows only certain light wavelengths to penetrate and reach the detector. Then, by comparing amplitudes of adjacent pixels, the color is calculated.

One disadvantage of conventional image sensors is size due to the number of pixels (photo-detectors) required to produce a quality image. Another disadvantage of conventional image sensors is the complex electronics involved in addressing each pixel (photo-detector).

SUMMARY OF THE INVENTION

In one embodiment, the invention combines a scanning system similar to a display-type raster scan with a single photodiode to create an image. By doing so, the invention provides an imaging device that is smaller than traditional imaging devices.

According to one embodiment, the imaging device of the invention includes a light source unit, a photo-sensor and a scanning assembly. The light source unit is fixedly mounted in the first end of an elongated sheath and is adapted for illuminating a target. The photo-sensor is mounted on the scanning assembly, also located in the first end of the elongated sheath, and is adapted to detect light energy from the target. The scanning assembly scans the target to enable the photo-sensor to detect light energy from each of a plurality of locations on the target. According to a further embodiment, the imaging device of the invention synchronously digitizes the output from the photo-sensor from each of the plurality of locations on the target to generate an image of the target. According to a further embodiment, the light source unit provides wide angle/divergent illumination. According to one embodiment, the light energy includes reflected light. According to another embodiment, the light energy contains fluorescent light.

According to another embodiment, the scanning assembly includes a platform movably mounted on a constant velocity pivot joint adapted for enabling the scanning assembly to scan the target with a photo-sensor in two directions. According to one embodiment, the scanning assembly is adapted to scan the target at a sweep frequency of greater than or equal to about 1 kHz. According to a further embodiment, the scanning assembly is adapted to scan a target at a sweep frequency above about 5 kHz. According to a further embodiment, the scanning assembly is adapted to scan a target at a sweep frequency above about 10 kHz. According to a further embodiment, the scanning assembly is adapted to scan a target at a sweep frequency above about 15 kHz. According to another embodiment, the scanning assembly is adapted to completely scan the target at a scan frequency of greater than or equal to about 2 Hz. According to a further embodiment, the scanning assembly is adapted to completely scan a target at a scan frequency above about 5 Hz. According to a further embodiment, the scanning assembly is adapted to completely scan a target at a scan frequency above about 10 Hz. According to a further embodiment, the scanning assembly is adapted to completely scan a target at a scan frequency above about 20 Hz. According to a further embodiment, the scanning assembly is adapted to completely scan a target at a scan frequency above about 30 Hz. According to a further embodiment, the scanning assembly is adapted to completely scan a target at a scan frequency above about 40 Hz. According to a further embodiment, the scanning assembly is adapted to completely scan a target at a scan frequency above about 50 Hz. However, various sweep and scan frequencies may be employed without deviating from the scope of the invention. According to a further embodiment, the scanning assembly includes electromagnetic actuators for controlling platform movement. According to an alternative embodiment, the scanning assembly includes piezoelectric actuators for controlling the platform movement. According to another alternative embodiment, the scanning assembly includes micro-electronic machine (MEMS) actuators for controlling the platform movement.

According to one feature, the MEMS actuators are fabricated in silicon, which is also a common substrate material for both photo-sensors and lasers diodes. The photo-sensor and/or the laser diode may be fabricated directly on the MEMS actuator plate using standard semiconductor processing techniques. This reduces the need for bonding discrete parts to the scanning platform, with the advantage that it may reduce the overall mass of the platform, allowing for higher scan rates and lower drive power. According to a further embodiment, the photo-sensor is a single pixel photo-sensor.

According to one embodiment, the imaging device includes an aperture oriented with respect to the photo-sensor and adapted for limiting light energy from the target from impinging on the photo-sensor. According to one feature, the aperture allows substantially only the light energy from one target location at a time to impinge on the photo-sensor. According to another feature, the aperture includes a fixed focal length lens.

According to an alternative embodiment, the imaging device of the invention includes a light source unit, a photo-sensor and a scanning assembly, wherein both the light source unit and the photo-sensor are movably mounted on a scanning assembly in the first end of an elongated sheath. The light source illuminates the target as the scanning assembly scans a plurality of locations on the target. The photo-sensor synchronously captures the light energy from each of the scanned locations on the target. The imaging device of the invention then synchronously digitizes the output from the photo-sensor from each of the plurality of locations on the target to generate an image of the target.

According to another alternative embodiment, the imaging device of the invention includes a light source unit, a photo-sensor and a scanning assembly, wherein the photo-sensor is fixedly mounted on a platform in the first end of an elongated sheath and the light source is movably mounted on a scanning assembly, also in the first end of the sheath. According to one feature of this embodiment, the scanning assembly scans the target to discretely illuminate each of a plurality locations on the target. According to a further feature, the photo-sensor synchronously captures the light energy from each of the illuminated locations. According to another feature the imaging device of the invention then digitizes the output from the photo-sensor from each location on the target to generate an image of the target.

According to one embodiment, the light source employs one or more LEDs. According to another embodiment, the light source employs one or more laser diodes. In a further embodiment, the light source unit employs a fixed focal length lens to focus the light onto discrete locations of the target. According to a further embodiment, the photo-sensor employs a wide angle lens to capture light energy from each of the scanned locations on the target.

According to a further embodiment, the first end of the elongated sheath forms a lens adapted for focussing the light from the light source on to each of the scanned locations on the target. According to another embodiment, the first end of the elongated sheath forms a lens adapted for focussing light energy from each of the scanned locations on the target back on to the photo-sensor.

According another alternative embodiment, the invention provides a scanning system having a light source and a photo-sensor, both located discretely from a first end of an elongated sheath to illuminate a location on a target. A beam splitter/combiner couples light from the light source through a fiber optic connection to an end of the fiber optic connection located in the first end of the elongated sheath. The beam splitter/combiner also couples light energy from the target through the first end of the elongated sheath and the same fiber optic connection to the photo-sensor. According to a further embodiment, the scanning system includes a scanning mechanism, located in the first end of the elongated sheath and adapted for moving the end of the fiber optic connection to scan synchronously light from the source onto each of a plurality of locations on the target, and to transfer light energy from each of the plurality of locations on the target back to the photo-sensor. According to a further feature, the scanning system of the invention synchronously digitizes the output from the photo-sensor due to each of the plurality of scanned locations on the target to generate an image of the target.

According to another embodiment, the invention provides a scanning system adapted for generating color images of a target. According to one embodiment, the scanning system of the invention employs field sequenced color (e.g., red, blue, green) LEDs pulsed in sequence for each of the plurality of locations illuminated on the target to achieve a color image of the target. According to one preferred embodiment, the imaging devices and methods of the invention are particularly adapted for analysis of living tissue.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing and other objects of the invention and the various features thereof may be more fully understood from the following description when read together with the accompanying drawings in which like reference designations generally refer to the same or similar parts throughout the different views and in which the depicted components are not necessarily drawn to scale.

DESCRIPTION OF AN ILLUSTRATIVE EMBODIMENT

As described in summary above, the invention, in one embodiment, is directed to a miniature imaging device. In one embodiment, the imaging device is located in the tip of an elongate sheath such as a catheter. The sheath may be inserted into a human body to observe images of target tissue. According to one embodiment, the imaging device of the invention is employed where conventional endoscopes are too large to be useful.

Figure 1A:
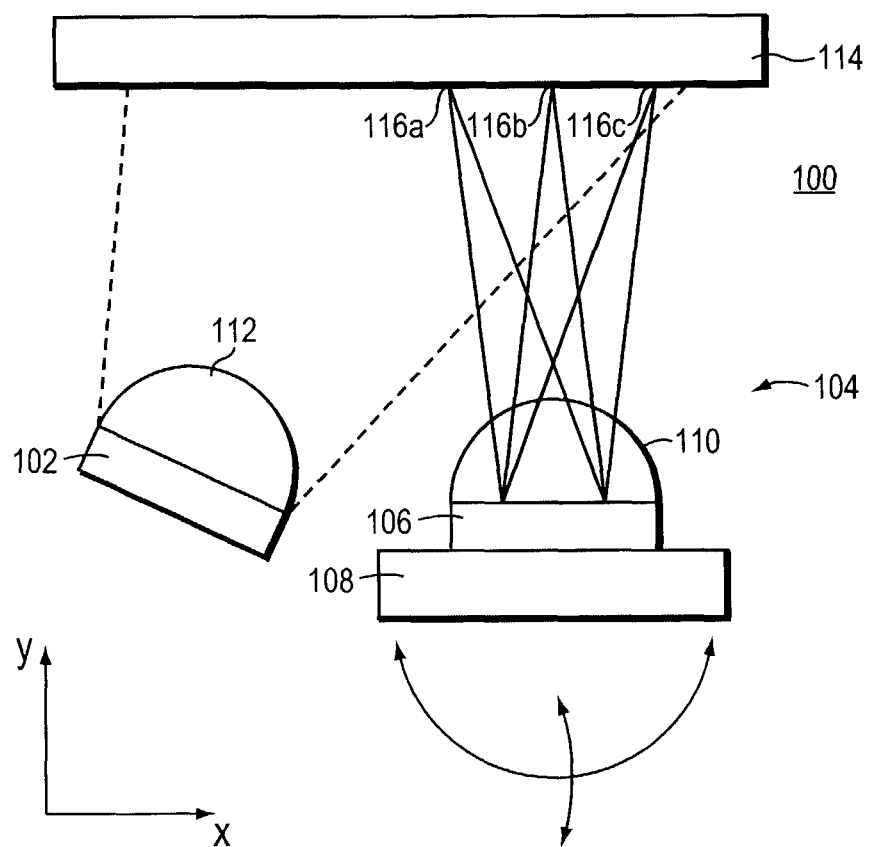
FIG. 1A is a schematic diagram depicting an imaging device employing a scanned detector, according to an illustrative embodiment of the invention.

FIG. 1A is a schematic diagram depicting an imaging device 100 employing a scanned detector, according to an illustrative embodiment of the invention. As depicted, the imaging device 100 includes a fixedly mounted light source 102 and a scanned photo-sensor assembly 104. The scanned photo-sensor assembly 104 includes a photodiode 106 mounted on a scanning device 108 adapted to move along two axes (x,y). The imaging device 100 also includes a wide angle lens 112 mounted relative to the light source 102 and adapted to focus light from the light source 102 onto an entire target 114. The scanning device 108 synchronously scans the photodiode 106 to receive light energy from each of a plurality of locations, such as the locations 116a-116c, on the target 114. A focussing lens 110, located relative to the photodiode 106 limits the light energy from the target from impinging on the photodiode 106. More particularly, the focussing lens 110 allows substantially only light from a particular one of the plurality of scanned target locations to impinge on the photodiode at any one time. Subsequent to scanning the entire target or a region of interest, the scanning device 100 digitizes the outputs from the photodiode 106 for synchronously captured images for each of the plurality of scanned locations on the target 114 to generate a high quality image of the target 114.

Figure 1B:
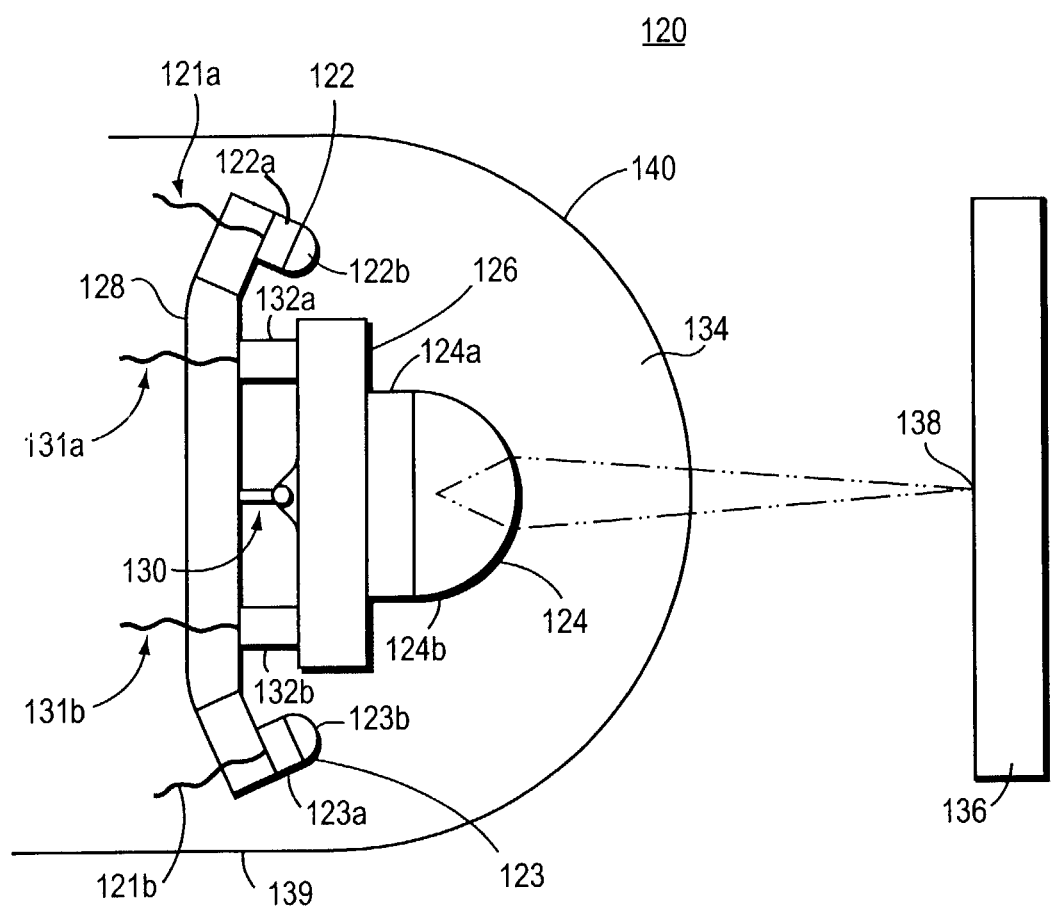
FIG. 1B is a schematic side view of an imaging device employing a fixed position light source and a scanned detector, according to an illustrative embodiment of the invention.
Figure 1C:
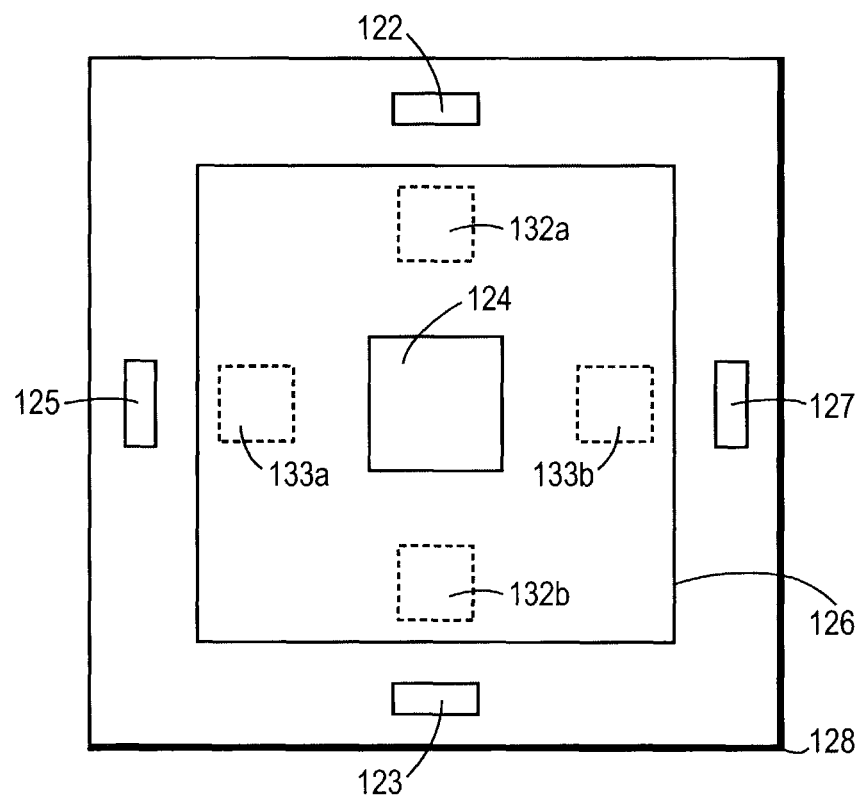
FIG. 1C is a schematic top view of the imaging device of FIG. 1B.

FIG. 1B is a schematic side view of an imaging device 120 employing a fixed position light source and a scanned detector of the type illustrated in FIG. 1A. FIG. 1C is a schematic top view of the imaging device of FIG. 1B. Referring to FIGS. 1B and 1C, the imaging device 120 includes four light source assemblies 122, 123, 125 and 127; a photo-sensor assembly 124, a platform 126; a base 128, a pivot 130; x-axis actuators 132a and 132b; and y-axis actuators 133a and 133b, all located in the end 134 of an elongated sheath 139. The light source assemblies 122, 123, 125 and 127 are all fixedly mounted to a front face of the base 128. Each of the light source assemblies include an LED and a wide angle lens adapted for illuminating the target 136. More specifically, the light source assembly 122 includes an LED 122a and a wide angle focussing lens 122b. Similarly, the light source assembly 123 includes an LED 123a and a wide angle focussing lens 123b; the light source assembly 125 includes an LED and a wide angle focussing lens; and the light source assembly 127 includes an LED and a wide angle focussing lens. Each LED is also powered by an LED power wire (e.g., 121a and 121b). According to one illustrative embodiment, the light source assemblies 122, 123, 125 and 127 may illuminate the target 136 with any frequency of light, either concurrently or in a sequenced fashion. In one illustrative example, the light source assemblies 122, 123, 125 and 127 may illuminate the target 136 with white light for black and white image generation, and sequenced red, green and blue light, for color image generation. However, any other combination of wavelengths may be employed without deviating from the scope of the invention. In other embodiments, for particular applications, such as scans that need to penetrate blood, the light source assemblies illuminate the target 136 with infrared light. According to one feature of the illustrated embodiments, each of the light source assemblies are mounted at an angle relative to the plane of the platform 126. Although the embodiment of FIGS. 1B and 1C depict four light source assemblies, any number may be employed, limited by size and power constraints.

The photo-sensor assembly 124 fixedly mounts on a platform 126. The platform 126, in turn, movably mounts the base 128 by way of a universal pivot joint 130. The universal pivot joint 130 enables the platform 126 to move in both the x and y-axes. The actuators 132a, 132b, 133a and 133b actuate the movement of the platform 126 with respect to the base 128. More particularly, the actuators 132a and 132b actuate the platform 126 along the x-axis and the actuators 133a and 133b actuate the platform 126 along the y-axis. In one embodiment, the actuators are processor controlled. According to one preferred embodiment, the actuators are electromagnetic. However, according to other embodiments, the actuators may be MEMs or piezoelectric actuators. Control signals are transmitted to the actuators 132a, 132b, 133a and 133b via scan control wires (e.g., 131a and 131b).

According to the illustrative embodiment, the actuators 132a, 132b, 133a and 133b actuate the platform 126 in a predefined pattern (e.g., spiral, circle, raster scan or the like) to scan the target 136 to enable the photo-sensor assembly 124 to detect light energy from each of a plurality of locations on the target 136. The detected light may be, for example, fluorescent or reflected light and may be from anywhere in the spectrum, including visible and infrared. In one embodiment, the actuators 132a, 132b, 133a and 133b are pulsed to cause the platform 126 to move. In a further embodiment, the actuators are operated at resonance to reduce the power necessary to actuate the platform. According to the illustrative embodiment, the photo-sensor assembly 124 includes a photo-sensor 124a (preferably a single photo-diode) and a focussing lens and/or aperture 124b. The focussing lens or aperture 124b limits the amount of light energy from the target allowed to impinge on the photo-sensor 124a. According to one feature, the lens/aperture 124b allows only the light energy from one target location at a time to impinge on the photo-sensor 124a. Optionally, the photo-sensor assembly 124 includes a mask on the photo-sensor 124a to further narrow the field of view (i.e., the selectivity). According to another feature, the lens is a fixed focal length converging lens. In one embodiment, the lens is a gradient index lens. According to another feature, the end 134 of the elongated sheath 139 forms or includes a lens 140 for assisting in providing light from the source assemblies to the target 136 and/or focussing light energy from the target 136 back to the photo-sensor 124a.

According to a further feature, the illustrative imaging device 120 synchronizes the motion with the capture circuitry and digitizes the output from the photo-sensor 124a for each of the plurality of locations (e.g., 138) on the target 136 to generate an image of the target 136.

According to one embodiment, the illustrative imaging device is about one millimeter square in size and provides about one hundred micron resolution.

Figure 2A:
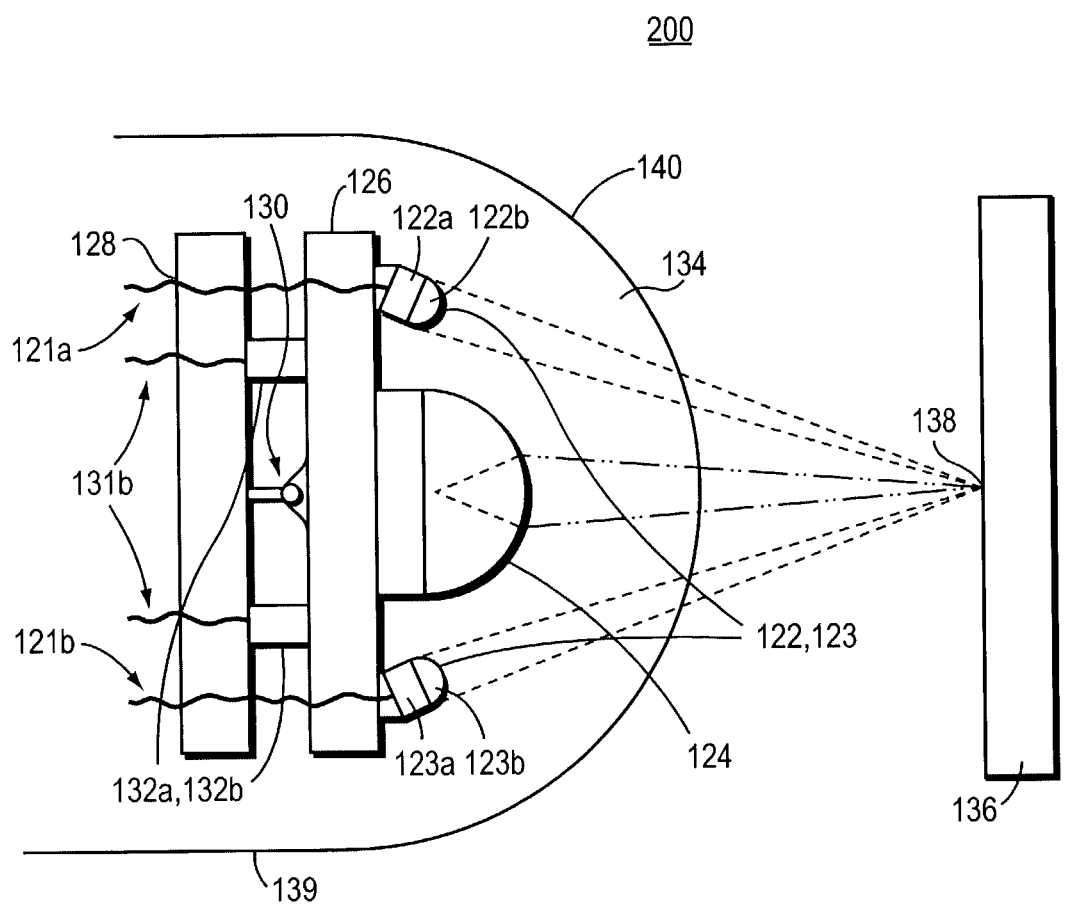
FIG. 2A is a schematic side view of an imaging device, employing a scanned light source and a scanned detector, according to an illustrative embodiment of the invention.
Figure 2B:
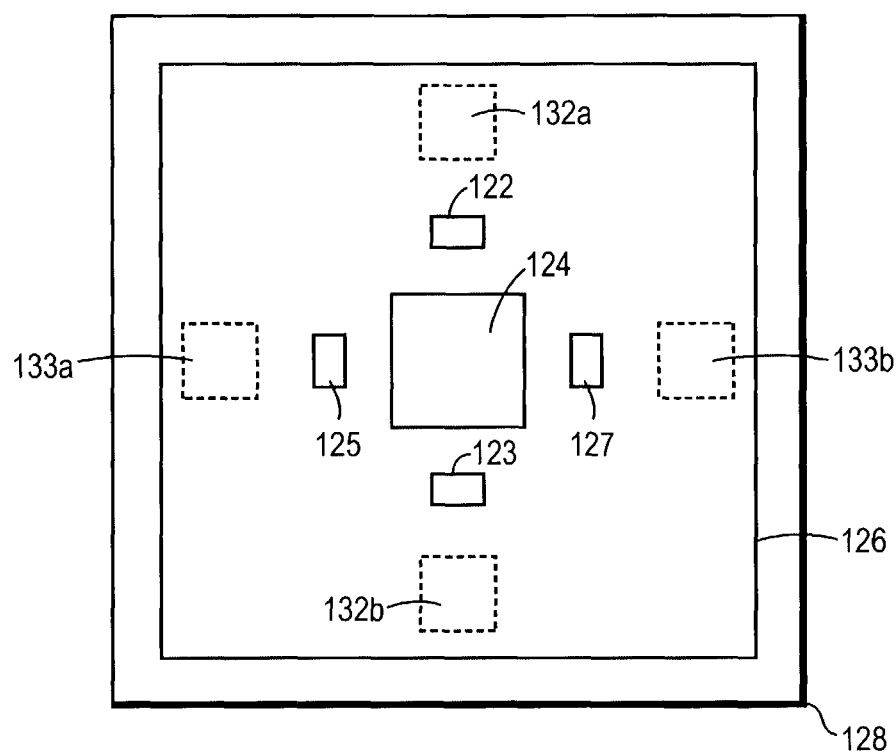
FIG. 2B is a schematic top view of the imaging device of FIG. 2A.

FIGS. 2A and 2B depict an alternative embodiment 200 of the invention, wherein both the light source assemblies 122, 123, 125 and 127, and the photo-sensor assembly 124 are mounted on the platform 126 and can thus be directed at each of a plurality of locations on the target 136. Rather than the wide angle divergent lenses employed in the embodiment of FIGS. 1B and 1C, according to the illustrative embodiment of FIGS. 2A and 2B, the light source assembly lenses (e.g., 122b and 123b) are fixed focal length lenses that focus light from the light source assemblies to each of the plurality of locations being scanned on the target 136. Other than this difference, the embodiment of FIGS. 2A and 2B operates in essentially the same fashion as the embodiment of FIGS. 1B and 1C.

Figure 3:
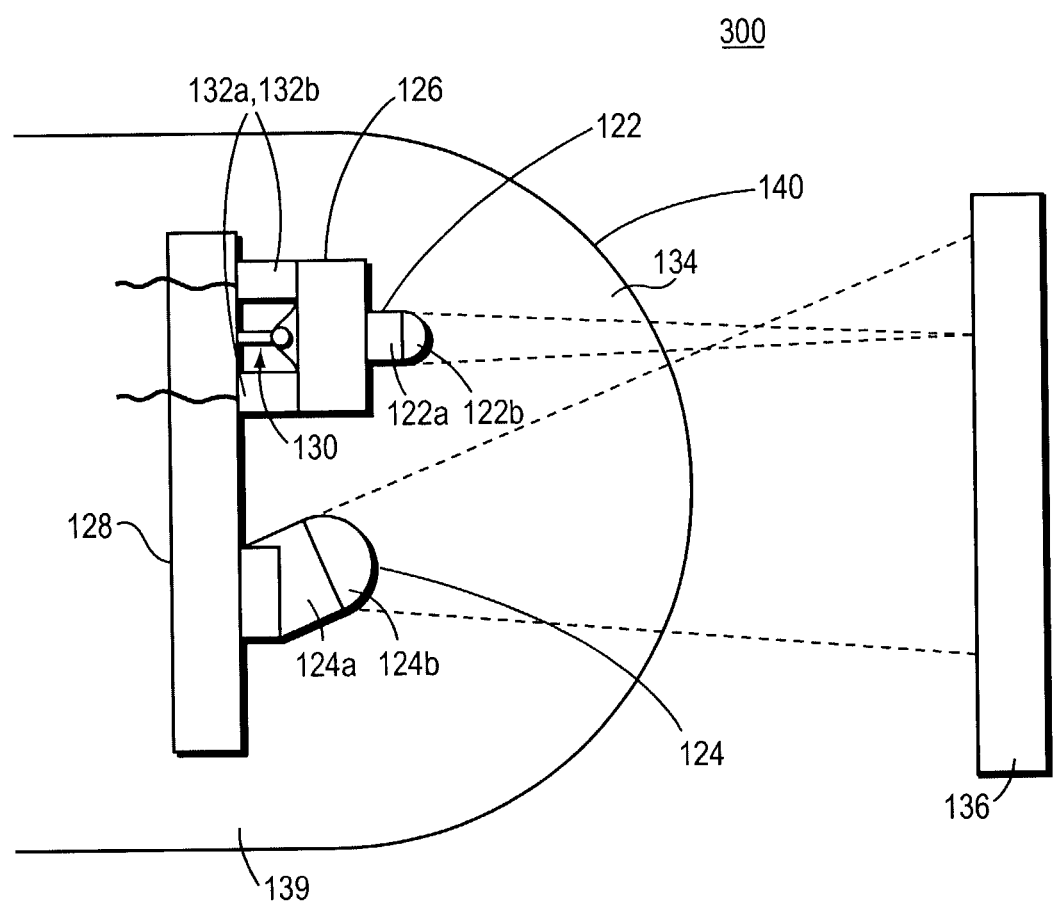
FIG. 3 is a schematic side view of an imaging device employing a scanned light source and fixed position detector, according to an illustrative embodiment of the invention.

FIG. 3 is a schematic side view of an imaging device 300 employing a scanned light source and fixed position detector, according to an illustrative embodiment of the invention. According to the illustrative embodiment of FIG. 3, the light source assembly 122 is fixedly mounted on the platform 126. As in the previous embodiments, the platform 126 is movably mounted to the base 128 by way of the universal pivot 130 and actuated by the x-axis actuators 132a and 132b and the y-axis actuators. The photo-sensor assembly 124 is fixedly mounted on the base 128 at a location adjacent to the platform 126. In this embodiment, the light source assembly 122 employs a fixed focal length lens 122b and the photo-sensor assembly 124 employs a wide angle lens 124b.

According to the illustrative embodiment of FIG. 3, the actuators actuate the platform 126 along the x- and y-axes in a predefined pattern (e.g., spiral, circle, raster scan or the like) to scan the target 136 to enable the light source assembly 122 to illuminate discretely each of a plurality of locations on the target 136 with, for example, white light for black and white image generation, or sequenced red, green and blue light, for color image generation. Although only one light source assembly is depicted in FIG. 3 and as discussed above, any number of light source assemblies may be mounted on the platform 126 without deviating from the scope of the invention.

According to the embodiment of FIG. 3, the photo-sensor assembly 124 includes a photo-sensor 124a (preferably a single photo-diode) and a wide angle lens 124b. The lens allows substantially all of the light energy from the target 136 resulting from the light from the source assembly 122 to impinge on the photo-sensor 124a. By synchronously scanning the light source discretely over each of a plurality of locations on the target 136 and digitizing the output from the photo-sensor 124a for each of the plurality of locations, the sensor device of FIG. 3 generates an image of the target 136.

Figure 4:
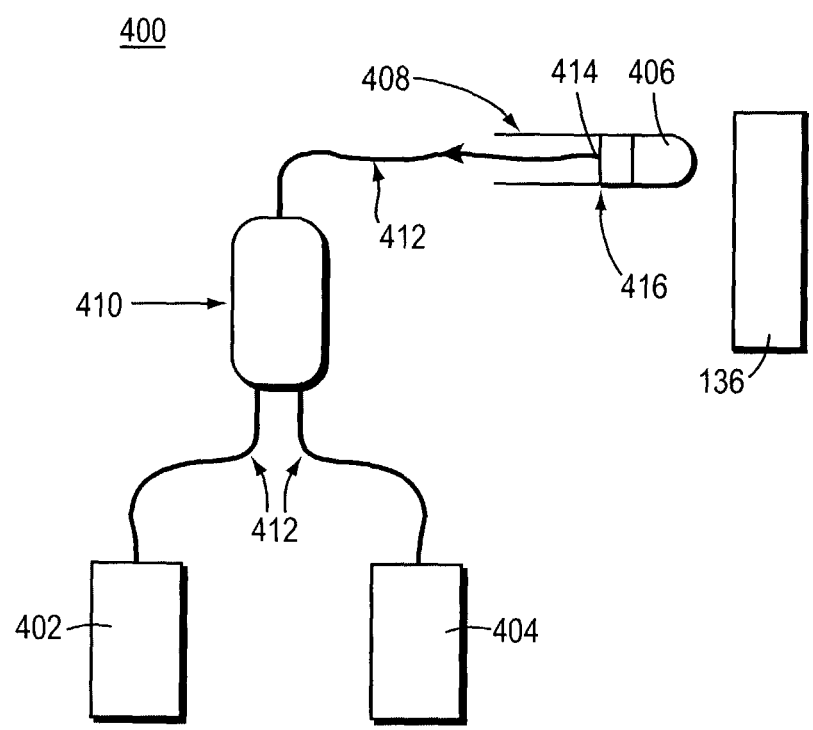
FIG. 4 is a schematic diagram depicting an imaging device employing a scanning device located remotely from a light source and a detector, according to another illustrative embodiment of the invention.

FIG. 4 depicts a photo-sensor system 400 according to an illustrative embodiment of the invention. The system 400 includes a light source 402 and a photo-sensor 404, both located discretely from a first end 406 of an elongated sheath 408 to illuminate a location on a target 136. A beam splitter/combiner 410 couples light from the light source 402 through a fiber optic connection 412 to an end 414 of the fiber optic connection 412 located in the first end 406 of the elongated sheath 408. The beam splitter/combiner 410 also couples light energy from the target 136 through the first end 406 of the elongated sheath 408 and the fiber optic connection 412 to the photo-sensor 404. According to the illustrative embodiment of FIG. 4, the scanning system 400 includes a scanning mechanism 416, located in the first end 406 of the elongated sheath 408, and adapted for moving the end 414 of the fiber optic connection 412 to scan synchronously light from the source 402 onto each of a plurality of locations on the target 136, and to transfer light energy from each of the plurality of locations on the target 136 back to the photo-sensor 404. According to one illustrated feature, the system 400 is configured for locating the light source 402 and/or the photo-sensor 404 remotely from the elongated sheath 408. According to a further feature of the illustrative embodiment of FIG. 4, the scanning system 400 synchronously digitizes the output from the photo-sensor 404 due to each of the plurality of scanned locations on the target 136 to generate an image of the target 136.

Although the above embodiments describe scanning the target directly, in alternative embodiments, a lens, such as the lens 140, may be employed for image reduction. Then, the reduced image may be scanned. In this way, the necessary excursion of the platform 126 and the scan time can be reduced.

Figure 5:
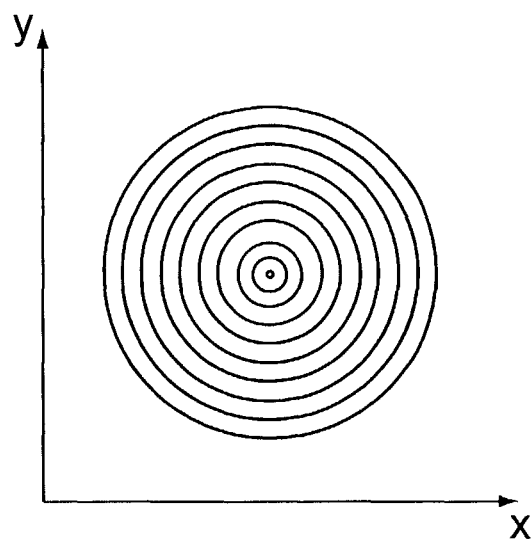
FIG. 5 depicts a pattern for a circular type of image scan, according to an illustrative embodiment of the invention.
Figure 6:
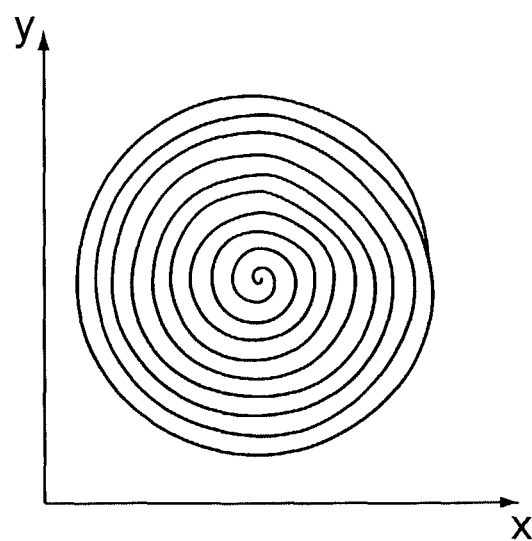
FIG. 6 depicts a pattern for a spiral type of image scan, according to an alternative illustrative embodiment of the invention.

FIG. 5 depicts a circular scanning pattern according to an illustrative embodiment of the invention. By starting in the center of the imaging area of the target, the image is acquired by moving the scanning device such that the scan produces a circular pattern with increasing diameter. The diameter increases until the end of the viewing area is reached. The scanned spot does not have to return to the center for the next frame. Instead, the illustrative imaging device of the invention acquires the data differently from that of the increasing diameter circle. The data is now acquired using a circular pattern with a decreasing diameter until the center of the imaging area is reached. In one embodiment, odd numbered frames use the increasing diameter scan, while even numbered frames use the decreasing diameter scan. The scanning device of the invention digitizes the information appropriately based on the phase of the scan pattern (i.e., increasing or decreasing diameter). The acquired data is essentially in polar coordinates $(r,\theta)$. The polar coordinates can be converted to Cartesian coordinates for image reconstruction. FIG. 6 depicts a spiral scan pattern according to another illustrative embodiment of the invention. According to other illustrative embodiments, polygonal scanning patterns, such as square scanning patterns are employed. It should be noted that any scanning pattern may be used without deviating from the scope of the invention.

Figure 7A:
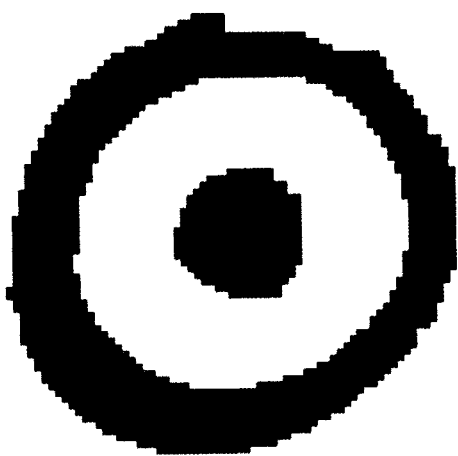
FIG. 7A depicts an image pattern used as a test pattern, according to an illustrative embodiment of the invention.
Figure 7B:
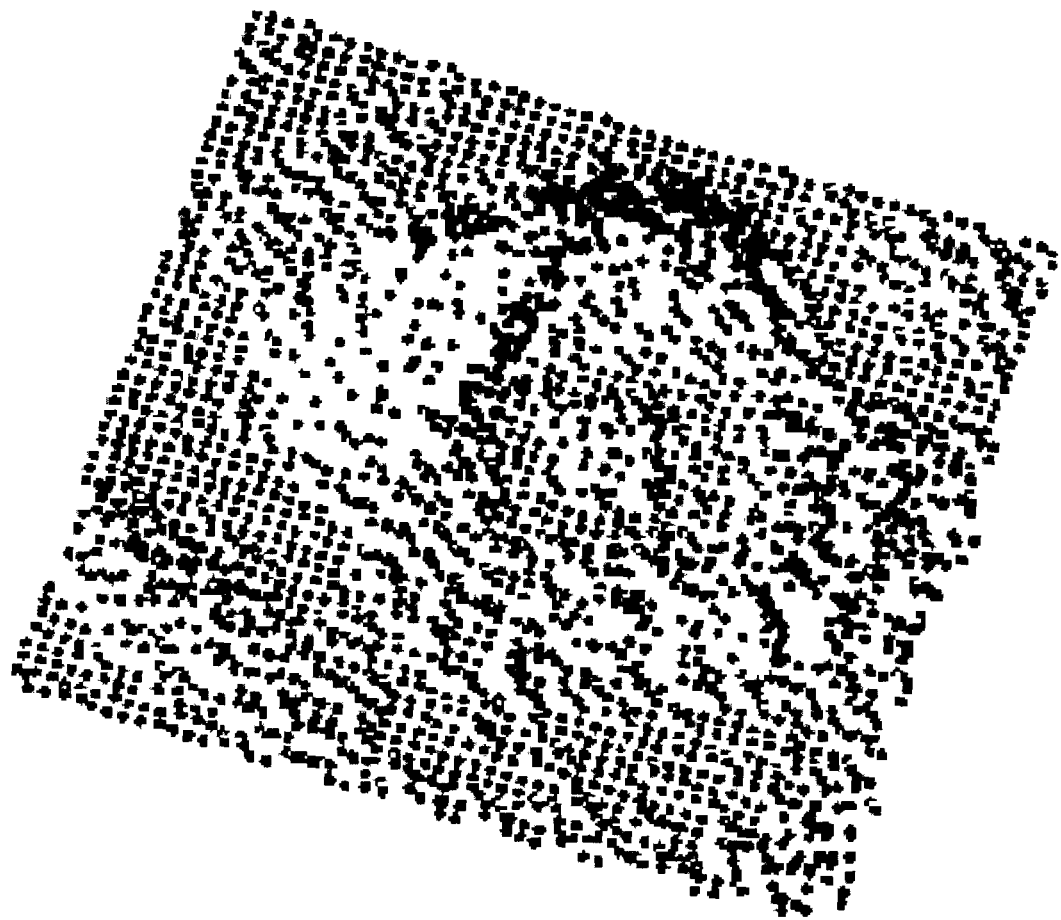
FIG. 7B depicts the image pattern of FIG. 7A as the image is seen by a single pixel scanning camera, according to an illustrative embodiment of the invention.
Figure 7C:
FIG. 7C depicts the image pattern of FIG. 7B as an amplitude color map, according to an illustrative embodiment of the invention.
Figure 8A:
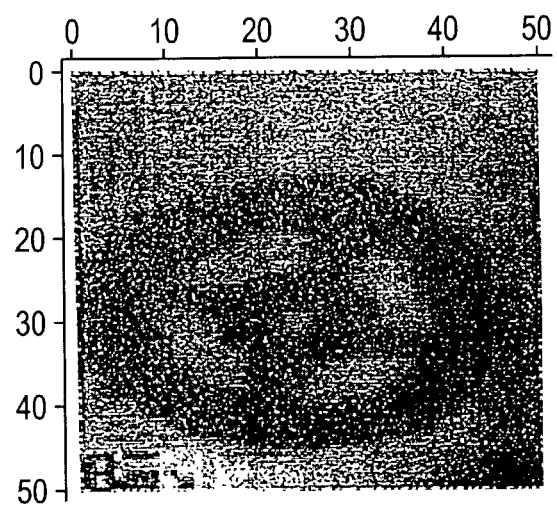
FIG. 8A is another illustrative scan of an image drawn on a piece of paper.
Figure 8B:
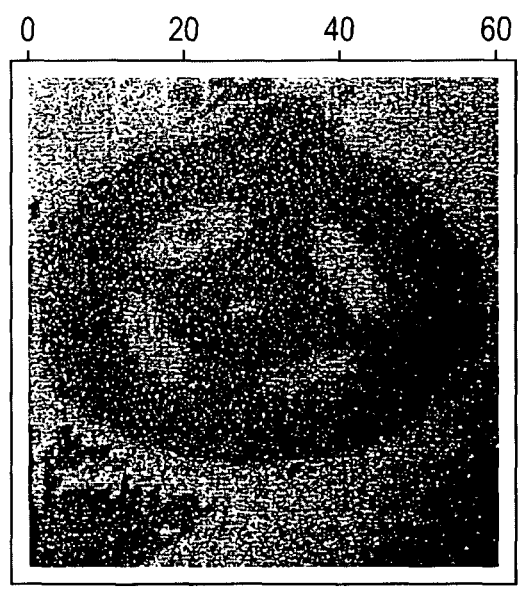
FIG. 8B is a scan of the same image of FIG. 8A with the addition of a tab to show orientation.

FIG. 7A depicts an image that was scanned with an actual device constructed in accord with the principles of the invention. FIG. 7B depicts the raw data in three-dimensional perspective corresponding to the image of FIG. 7A and generated by an illustrative embodiment of the invention employing a single pixel photo-sensor. FIG. 7C is amplitude color map corresponding to the image of FIG. 7A and generated by an illustrative embodiment of the invention employing a single pixel photo-sensor. FIG. 8A depicts another example of a scanned image generated by an illustrative embodiment of the invention. In FIG. 8A, dimensions are shown on the x- and y-axes in millimeters. FIG. 8B depicts another example of a scanned image, wherein the image includes a tab to show orientation. In FIG. 8B, dimensions are shown along the x-axis in millimeters.

As can be seen from the above illustrative embodiments, the invention provides a photo-sensor device that is inexpensive to manufacture and smaller than the current technology. In one embodiment, the invention employs a single miniature detector as opposed to an array of detectors, or bundles of fibers. One problem solved by the invention is that it can go into areas of the human body that an endoscope cannot. Additionally, since the device of the invention is inexpensive to make, it can be disposable. Additionally, the devices of the illustrative embodiments may be employed with any available display technology.

What is claimed is:

1. An imaging device insertable into a human body comprising:
   a sheath;
   a light source mounted on a first platform and disposed within the sheath for illuminating at least a portion of a target region;
   a photo-sensor mounted on a second platform and disposed within the sheath for sensing light energy received from at least a portion of the target region; and
   a movable assembly adapted to move the first platform in at least two dimensions relative to the target region.

2. The imaging device of claim 1 wherein the first and second platforms are the same platform.

3. The imaging device of claim 1 wherein the movable assembly is further adapted to move in at least two dimensions relative to the target region.

4. The imaging device of claim 1 further comprising a plurality of light sources disposed for illuminating at least a portion of a target region.

5. The imaging device of claim 4 wherein at least one of the plurality of light sources is an LED or a laser diode.

6. The imaging device of claim 1 wherein the sheath further comprises an aperture adapted for focussing light on the target region.

7. The imaging device of claim 6 wherein the aperture comprises a divergent lens or a fixed focal length lens.

8. The imaging device of claim 1 wherein the light source provides reflected light or fluorescent light.

9. The imaging device of claim 1 wherein the photo-sensor is a single pixel photo-sensor.

10. The imaging device of claim 1 wherein the sheath further comprises an aperture adapted for focussing light energy received from each of a plurality of illuminated locations of the target region onto the photo-sensor.

11. The imaging device of claim 10 wherein the aperture comprises a fixed focal length lens or a diverging lens.

12. The imaging device of claim 1 wherein the movable assembly comprises an electromagnetic material.

13. The imaging device of claim 1 wherein the movable assembly further comprises an electromagnetic actuator, a microelectronic machine (MEMS)-type actuator or a piezo-electric actuator coupled to the movable platform for controlling movement of the first platform.

14. The imaging device of claim 1 wherein the imaging device is disposable.

15. A method for imaging a target region inside a human body comprising:
   positioning a sheath relative to the target region inside the human body;
   illuminating at least a portion of a target region with a light source disposed within the sheath;
   sensing energy received from at least a portion of the target region with a photo-sensor disposed within the sheath; and
   moving the photo-sensor in at least two dimensions relative to the target region with a movable assembly.

16. The method for imaging of claim 15 further comprising:
   scanning the target region by moving the photo-sensor in at least two dimensions.

17. The method of imaging of claim 16 further comprising:
   mounting the movable assembly on a constant velocity pivot joint adapted for moving the photo-sensor in two dimensions.

18. The method of imaging of claim 16 further comprising:
   scanning the target region at a sweep frequency of greater than or equal to about 1 kHz.

19. The method of imaging of claim 16 further comprising:
   scanning the target region at a rate of greater than or equal to about 2 Hz.

20. The method of imaging of claim 15 further comprising:
   providing a light source of field sequenced color LEDs pulsed in sequence for each of a plurality of locations of the target region; and
   scanning the target region by moving the photo-sensor in at least two dimensions to generate a color image of the target region.

21. The method of imaging of claim 15 further comprising:
   scanning the target region by moving the photo-sensor in two dimensions to create a raster scan or a circular scan of the target region.

22. The method for imaging of claim 15 further comprising:
   synchronously digitizing the sensed energy received by the photo-sensor from each of a plurality of locations of the target region to generate an image of the target region.

23. The method for imaging of claim 15 further comprising:
   synchronously scanning light from the light source onto each of a plurality of locations on the target region.

* * * * *

UNITED STATES PATENT AND TRADEMARK OFFICE
CERTIFICATE OF CORRECTION

PATENT NO. : 8,423,110 B2  
APPLICATION NO. : 10/195603  
DATED : April 16, 2013  
INVENTOR(S) : Louis J. Barbato It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3277 days.

Signed and Sealed this
Tenth Day of December, 2013

Margaret A. Focarino
*Commissioner for Patents of the United States Patent and Trademark Office*